US007785570B2

(12) United States Patent
Jacobs et al.

(10) Patent No.: US 7,785,570 B2
(45) Date of Patent: Aug. 31, 2010

(54) COMBINATION VACCINE FOR POULTRY

(75) Inventors: Antonius Arnoldus Christiaan Jacobs, Kessel (NL); Paul Cornelius Maria van Empel, Ottersum (NL); Petrus Johannes Maria Nuijten, Sambeek (NL)

(73) Assignee: Internet International B.U., Boxmeer (NL)

( * ) Notice: Subject to any disclaimer, the term of this patent is extended or adjusted under 35 U.S.C. 154(b) by 958 days.

(21) Appl. No.: 10/582,315

(22) PCT Filed: Dec. 21, 2004

(86) PCT No.: PCT/EP2004/053623

§ 371 (c)(1),
(2), (4) Date: Jun. 8, 2006

(87) PCT Pub. No.: WO2005/063284

PCT Pub. Date: Jul. 14, 2005

(65) Prior Publication Data

US 2009/0053262 A1 Feb. 26, 2009

(30) Foreign Application Priority Data

Dec. 23, 2003 (EP) .................................. 03104954

(51) Int. Cl.
*A61K 49/00* (2006.01)
*A61K 39/38* (2006.01)
*A61K 47/00* (2006.01)

(52) U.S. Cl. ...................... 424/9.2; 424/9.1; 424/184.1; 424/199.1; 424/200.1; 424/201.1; 424/234.1; 424/235.1; 424/278.1

(58) Field of Classification Search .................. 424/9.1, 424/9.2, 184.1, 199.1, 200.1, 201.1, 204.1, 424/234.1, 235.1, 278.1
See application file for complete search history.

(56) References Cited

U.S. PATENT DOCUMENTS

2003/0149255 A1 8/2003 Lopes et al.

FOREIGN PATENT DOCUMENTS

WO WO 94/09114 4/1994

OTHER PUBLICATIONS

Lopes, V., et al. Avian Diseases, vol. 46, pp. 177-185, 2002.*
Buchmeier, N. et al. “Recombination-deficient mutants of Salmonella typhimurium are avirulent and sensitive to the oxidative . . . ” Molecular Microbiology, 7(6): 933-936 (1993).
Guerry, P. et al, “Development and Characterization of recA Mutants of Campylobacter jejuni for Inclusion in . . . ” Infection and Immunity,62(2): 426-432 (Feb. 1994).

* cited by examiner

*Primary Examiner*—Rodney P. Swartz
(74) *Attorney, Agent, or Firm*—William M. Blackstone; Aaron L. Schwartz

(57) ABSTRACT

The present invention relates to a combination vaccine for the protection of poultry against *Ornithobacterium rhinotracheale*, to the use of a live over-attenuated *Ornithobacterium rhinotracheale* strain and a live attenuated poultry virus for the manufacturing of such a combination vaccine, to methods for the preparation of said combination vaccine and to vaccination kits for the immunization of poultry against *Ornithobacterium rhinotracheale.*

15 Claims, 8 Drawing Sheets

Figure 1:
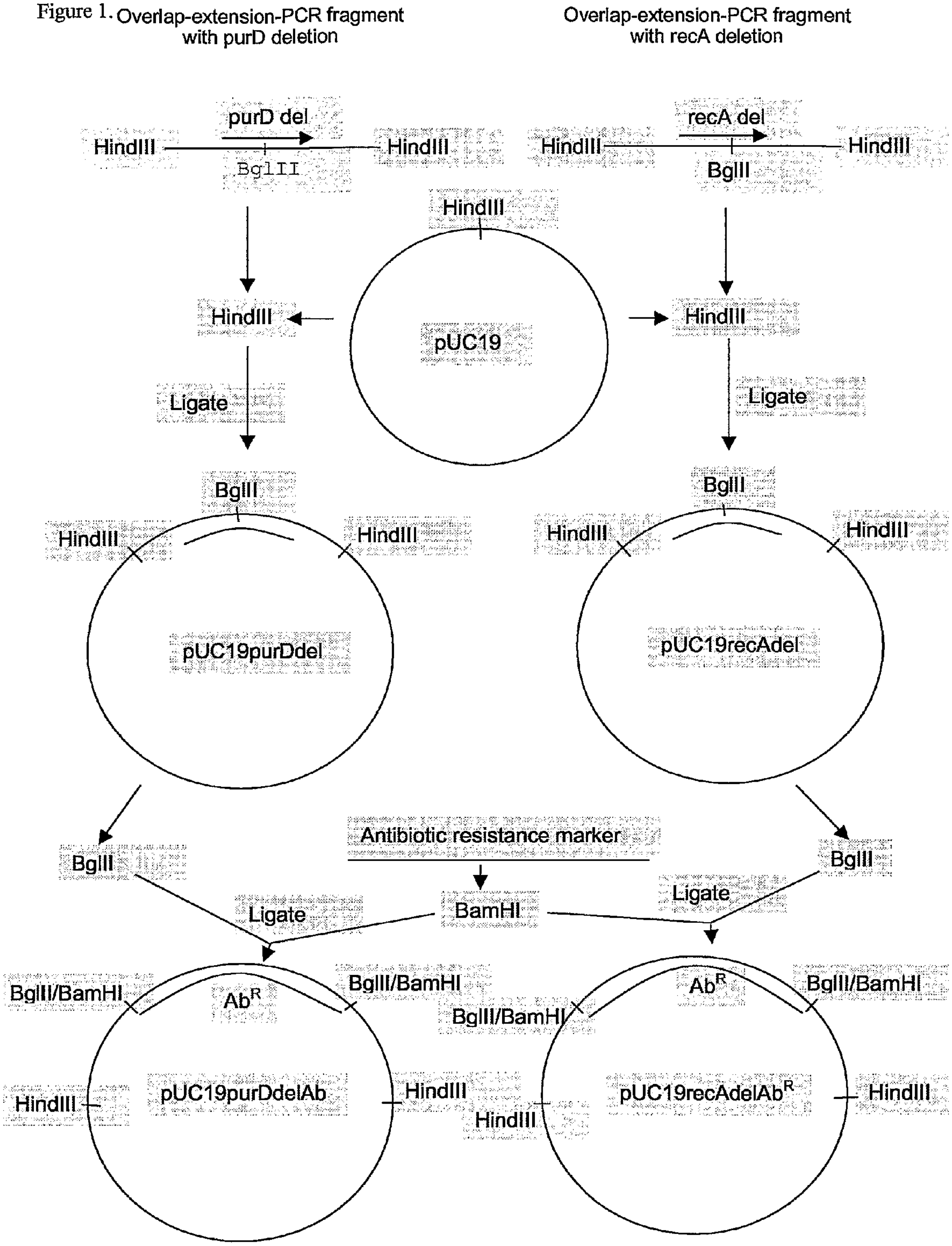

Figure 2A.

```
   1  GTTCGACCAA ACGGCTTGTT GTGCGGTGAA ACATAGCACT CCTTGTGGCG TGGCTTTAGA TGATGATATT TTGCAAGCGT
      >>.......F5........>>          CTTAAGCTTGGA>>.......F13........>>
                                        ------
                                       HindIII

  81  ACCAAAAAGC ACACGACTGC GACCCGATTT CGATTTTTGG TGGCATTGTA ACTTTTAATA AAAAAGTAAC AAAAGCAGTG

 161  GCAGAAAAAT GTAACGAGAT TTTCCTTGAA ATCGTTGCTG CACCGAGCTT TGAGCCAGAG GCTTTGGAAG TTTTTGCTAA

 241  AAAGAAAAAT TTGCGCGTGA TTGAAGTTAA AAATCCATTA AGCGATAAAA TGCAACTCGT GCAAGTAGAT GGCGGATTGC

 321  TCGTGCAAGA AATCGACAAA TCGTTTAGCA ATGATTTTAA AGTAGTAACC GAAAAACAAC CTACCGAAAA GCAACTTTCT

 401  GATTTGGAAT TTGCCATGAA AGTAGTGAAA CATGTAAAGA GCAATGCCAT CGTGGTTGCC ACAAACGGAC AAGCTCTAGG

 481  CGTGGGCACA GGCGAGACTA ATCGTATTTG GGCAGCACAG CAGGCGATTC AGCGTGCAAA GGAAAAAACA CAAGAAAATC

 561  TAGTTTTGGC TTCCGATGCC TTTTTCCCAT TCAGAGATGT GGTAGATTAT GCAGCACAAG AAGGCATTAC AGCCTTGATT

 641  CACCCAGGAG GAAGCATGCG CGACCAAGAG AGCATAGACG CGGCTAATGA ACACGGAATC CCGATGATCA TCAGCGGTAT

 721  GAGACATTTC TTACATTAAA TCAAAAAATC TAAACAATAA TTATCAATAA TTCTAAAACA CAATAAGTAT GAATGCAAAT
                                                                              >>...purD...>

 801  GATTACAAAA AAATACTCAT CGTAGGAAAC GGCGCAAGAG AACACGCCAT CGGGTGGAAA ATTAAACAAG ACCACCCTTC
      >....................................purD.........................................>

 881  TTGCGAGCTT TTCTTTGCGC CAGGAAACGC TGGAACCGAA CAAATTGGAA AAAACATCGT AGCTGAATCT AATTATGGCT
      >....................................purD.........................................>
                                <<........OE-R..........<<AGATCTGGCGCTACGCTAGAAG
                                                          ------
                                                          BglII

 961  TAATGCTTTT TGCTCAACAA AATGATATAG ACTTAACGAT TGTAGGTCCA GAAGCAGAAT TGGTAGAAGG TATTGTAGAC
      >....................................purD.........................................>

1041  TTGTTTGAAT CCAATCAATT AAGAATTTTT GGTCCAGATA AGCGTGCGGC TAAATTGGAA GGCAGCAAGG CTTTTGCCAA
      >....................................purD.........................................>

1121  AGATTTTATG GAGAAATACG GCGTGCGCAC GGCTTTTGCC AAAAGTTTCA ACAATTTTGT AGACGCTAGA GATTATGTAA
      >....................................purD.........................................>

1201  AAGAGCTCAC GCAATTCCCT ATCGTGATCA AAGCCAGTGG CTTGGCAGCA GGAAAAGGTG TGATCATCGT GCACNTACAA
      >....................................purD.........................................>

1281  CTTGAAGCCG AAACTACTTT GCGCAAAATC ATGGAAGACA AAACCTTTGG CGAAGCAGGC AACGAGGTCG TAATCGAGGA
      >....................................purD.........................................>

1361  ATACTTAAAA GGTGTGGAAG TTTCTGTGCT TTCTATCTTT AACCATAAAG AAATTAAAAC TTTCTTGCCT GTAAAAGACC
      >....................................purD.........................................>

1441  ACAAGAAAAT CGGAAAAGGC GAAACAGGAC TCAACACGGG CGGAATGGGC GTAGTGGCTC CTAACCCGCA TTTTACCGAT
      >....................................purD.........................................>

1521  GAGCACATGA AGGAGTTTGA GAAAAACATT TTGCTCCCAA CACAAAAAGG GCTCTTGGCA GAAAAAATGC ATTTTGCAGG
      >....................................purD.........................................>

1601  CATTATTTTC TTTGGGCTTA TGATTACCGA GCATGGTATT TATCTATTGG AATACAACAT GCGATTTGGC GACCCAGAAA
      >....................................purD.........................................>

1681  CCGAAGCACT TTTGCCTTTG ATGGAGAATG ATTTAGTAGC CCTCATCGAT TCCGCAATAC ACCAGCAAGA CATTGAACTT
      >....................................purD.........................................>

1761  AAATGGAAAA ACGAACATGC TTGCTGTGTA GTAATGGCGA GCGGTGGCTA CCCAGGCACT TACGAAACTG GTTTTGAAAT
      >....................................purD.........................................>
```

Figure 2A continued

```
1841  CCGAGGATTG AACAAAGTTG ATGTTCCCGT ATTTATTGCA GGAGCCAGAG AAGAAAGTGG AAAAATCTAC ACCACAGGCG
      >.....................................purD.......................................>

1921  GGCGCGTGCT CAATGTGGTG GGAACTGGCG CTACGCTAGA AGAAGCCAGA AAAGTGGCTT ACGAAAATAT CCATAAAATC
      >.....................................purD.......................................>
                            GAGATCTGG>>......OB-F.......>>
                             ------
                             BglII

2001  AATTTTGATT ATGAATATTA TCGCGAAGAC ATCGGGAAGA TATAATCTCG CTGATTTTTA ACCAAAACAT ATTTAAAAAC
      >....................purD....................>>

2081  GCTTTTGTTA CTTTTATAAA CAAAGGCGTT TTTCTATTTT TGTGCCACTA TAACATGATT TAACCCATGA AAAAAATACT

2161  AAAAATACTC ATTTTTCTAC TGCTCATTCC TTGGGTTTAT GCCCTGATTT TAATCTTTAT AAATCCACCT ATCACCATTA

2241  CACAGCTGAG CAATTTATCT TATGGTTTCT CCAGAACACA GCTCGCTTAT GATGAAATTC CGGCTAGTGC TAAATGGGCT

2321  GTAATTGCAG CAGAAGACCA GAATTTTGCC ATTCATAATG GCTTTGATTT TAAAGAAATT AAAACCGCCT ACGAGAAAAA

2401  CAAAGCGGGC AAGAAATTGC GTGGCGGGAG CACCCTTTCG CAACAAACTG CCAAAAATGT ATTTTTGTGG CAAGGGCGCA

2481  CTTGGATTAG AAAAGGATTG GAAACCTACT GCACCTTTAT CATCGAAACG CTGTGGAGCA AGGAGCGTAT TTTGCAAGTT

2561  TACCTCAACA ATGCCGAAAT GGGCAAAGGC GTTTATGGCA TAGAGGCAGC GGCGCAATAT TATTTTAAGA AAAACGCCTC

2641  ACAGCTCACG CCTACCGAGA CGGCACGCAT CATTGCCTGC CTGCCCAATC CCAAAAAATA CAATNTAAAC CCGCCAAGTG

2721  CCTACATCTC AAAACGCGGA CAATGGATTC TGCGCCAAGT GCGAAACTTG AAAGGCGATA GGGCTCTGAG CGAGATTGTG

2801  AACACGCCCT AACGCCTGCC TCAACTCTTT GCACACAGTT TACCAACTCT CTGCGAAGAG TTCACAAACT CTTCGCACAC

2881  ACTTCCCCAA GTCTTTGCAA AGAGTTGGGA GATACTTAGG CACAAAAAAA AGGAACCTCA TGAATAGAGG TTCCCTCTTC

2961  CTTAAAAGGA ATAAATAATA ATGTTTTTTA AGCTTTAGGC TTGGCTACTT TTTCAAAGCC TGCTGCCTTC ATGCTATCTA
                                      -------
                                      HindIII

3041  GGATACGCTT GCCTGGGCGG TAGTTTACGC CTACCTTTTT GATTAAGCCC GAATGAAAAT CTTTCTCTGT ATCTGCCGCT
                                                                           <<......R8......<

3121  CCACTGCTTA AAGTGGCATA GAGCGAGCCA AGCTTATCTA AACGAACGAT TTTGCCCGCT GCCAAGGCGT CTTGAATTAC
      <R8.<<AAGCTTAAG
         ------                       -------
         HindIII                      HindIII

3201  ATTCTCTAGC GCAATGATAA CGCCACGAAT ATCTGCCTCG CTGAGTGCCG AAAACTTCTC GATTTGCTTA ACGAGCTGGT

3281  CTATATCCAT TTCTCCATCG CTTGCCACCA CGGCATAGTA TTTTTGTGGC TCCCCTGGCT TGCTTGGGTT TCTACGCTGA

3361  ATTACATTGT ATTTTATGCT CATAATTACT CTATTTTTAA TAGCCTCCCG ATGGATATAA AGTTACGCTA CAATTAGGGT

3441  CTCCATAAGC AAATCTATAC CCCTCTCTTT CATATTCCCT TCTCATTCTT CTTGCTCCAT CTCTCAAGGC ATCCGCTCTA

3521  TTACTGCTAT ACCCCTCCTG AAGAAATGTG TCTGCACTTG AAGAAGAATA TGAAGAGCTA TGAGAATCGT GCAACATAGT

3601  CCAAGCTCCA TCTTGAGCTA TAACATTTGC ATGACATGTA ACACCTATAG TATAATAAAA TCTCCTAGGA GGTTGTGTTC

3681  CACCACCACC TCCAGAGCTA CTACTTTTTT TACATTGTCC ATTTTGGTTA GCATGATTTT GTCCGCCATC ACTTACTAAC

3761  TTCTTAGCTT CTGCTAAGGC TTTTTCTCTT GCTTTCTTTT CAGCATCTGC TTGGCTAATT CCACTCACTG CTGTAGCTGT

3841  CGCTTCTTTT TTATAGTTTA CCGAGGTTCC ATAATAGCCA CTACTACAAT TGTTTCTTGT AAAGTTTTTA TTAAAAGATT

3921  GAGTTTGTGT TGAGGTGTAC CCTCCGAAAC CTTTTACTTC TACAGTAAAG GTAGAACTCC CCATGCTTAC GGGGAAGGTG

4001  GCGATAGTAT ACGATTGCCC TGCCGGCATT TGTTTTACTT GATACACTCC ATCTCCTCCC ACTTCTATGC TTGCCGTTAA
```

Figure 2A continued

4081 ATTACCACTA CCGCTAAAAG AGCCTTCTGC TATTTTTAGT GTTAAATCAT TTATATCCCC TCCTTGTCCT TTTGCAGAAG

4161 CTTTTGTTAC ACTTACAGCA TCATAAGCTC CTTTTCCATT GGTATAAGGT ATTTATATGG CCAAAC

Figure 2B.

```
1     TAAAGCTGTA AWTCGCTATA AACGCCCTTT AGGATAAAAT CTGCCATTTT TTGCAGTATT TTWATAGCTA AAATTTAGAA
                                 >>.......FrecAOR1.......>>

81    AACACCATCT CGAGTAAAGG AGCGTGTAGT GCTCGCCATC GTTGAGCGAT TGCCCACCCT CAATTGATTT GGGCGAATAC
                 CTTAAGCTT>>.........F6.........>>
                   ------
                  HindIII

161   TTGAAATAAA TGGCATCTTC TAGCGACACA TTTTGCGCAG AAATCATGCA AAAAGCCCCG CATAAAAAGC TGAATAAAAA

241   WGCTAWTYTT CTTGTTTAAA AAAACTCATA AATTCCCCCA AATATAGAAA TATTCTGTGA AAAGTTGCAA TTTATTAACA
                                                                                     <<...<
321   CTATGTGCTT GCTTTTAATG AAAAAAGTAG ATTATTTTTC CGAATCCGAA AGTTTATTTA CGCCCCATCC GATGCCTAGT
      <..FrecA-4...<<

401   CCCMSCGATA GCCATGATTA ATACAAATAC AATTAAATCA WATTTTTCMC MTWWACCATA GCACAACACT TGCTAGCTCA

481   ACGAGTACTA GAGTGGTAAA AAGGATTTTT TGACGATTAT TCATGATTTT ATTTTTCTCA AAGGTAAATA TTTTAAACCA

561   TAATTTCACA AATCTTAAAA TCTATTTAAA TAATAGAGAA ACCAGAAAAA AATCGTATTT TTACGGAATG AATAAAATGT

641   TACAAGTAGG CGATAAAATG CCCGATTTCA AAGGTGTAGA CCAATTTGGG AAGGAGCATT CATCTGCCGA TTTCAAAAAT

721   CAGAAATTAG TCGTTTTTTT CTACCCAAAA GCCAGTACGC CAGGTTGCAC GGCAGAGGCT TGCAACATCA ACGATAATCT

801   TGATGCGCTA AAAGCACAAG GCTACCAAGT GATAGGCGTG AGTGCAGATT CGGTAGAAAA ACAACGAAAA TTCAGTGATA

881   AATACGATTT TAAATTCCCT GTGATTGCCG ATGTGGATAA GAAAATTATT GAAGCATTTG GCGTGTGGGG CGAAAAGAAA

961   TTCATGGGTA AAACCTATGA CGGAATTCAT CGTACGACAT TCATTATTGA TGAAAACGGA GTGGTGGAGC GCGTGATAGA
                             >>.......F7.......>>
                                   ------
                                   EcoRI

1041  AAAAGTGAAA ACAAAAGATC ATACCAATCA AATTTTAAAT TCAGAAAAAT AAAAATATGA GCGAAATAGA CGAAGCGAAA
                                                                >>.........recA..........>

1121  AGGAAAGCAC TCCAGCTAGT GCTTGATAAA ATGGACAAAA GCTATGGTAA AGGTGCCGTG ATGATGATGG GCGACAAAGC
      >.....................................recA.......................................>
                                                                  <<.........OER1.........<

1201  CATAGACGAA AATATTCCAG TAATCCCTAC GGGGTCTCTA GGTTTAGATT TAGCCTTGGG CGTGGGAGGG TATCCGCGCG
      >.....................................recA.......................................>
      <CGAGATCTCGTGCGTGCGGT
         ------
         BglII

1281  GTAGAATCGT GGAGATTTAC GGTCCAGAAT CTTCTGGTAA AACCACTTTG GCAATTCATG CCATTGCCGA AGCTCAAAAG
      >.....................................recA.......................................>

1361  TCTGGCGGAA TTGCAGCTTT CATCGATGCA GAGCACGCAT TTGATAGATA TTACGCAGAA AAATTAGGCG TAGATGTTGA
      >.............................................      --------------------------------->

1441  GCATTTAATT ATCTCTCAGC CAGATAATGG GGAGCAAGCT TTAGAAATTG CCGATAACTT AATCCGTTCA GGTGCAATTG
      >.....................................recA.......................................>
                                           ------
                                          HindIII

1521  ATATTATTGT AATCGATTCG GTAGCGGCTT TAACGCCAAA GTCGGAAATC GACGGAGATA TGGGCGATTC CAAAATGGGA
      >.....................................recA.......................................>

1601  TTGCAAGCGC GTTTGATGTC TCAAGCCTTG AGAAAGCTCA CGGGAACTAT CAATAAAACC AAATGTACTG CTATTTTCAT
      >.....................................recA.......................................>
```

Figure 2B continued

```
1681  CAACCAATTG AGAGAGAAAA TCGGTGTGAT GTTCGGTAGT CCAGAAACCA CAACGGGTGG TAATGCACTT AAATTCTATG
      >...................................recA.....................................>

1761  CATCGGTGCG TCTAGACATT CGTCGTTCTA CTCAGATTAA AGATGGGAAC GATGTCATCG GAAACTTGAC TCGCGTAAAA
      >...................................recA.....................................>

1841  GTAGTGAAAA ACAAAGTAGC TCCGCCATTC CGTAGTGCAG AATTCGACAT TATGTATGGC GAAGGAATCT CTAAAGCAGG
      >...................................recA.....................................>
                                           -------
                                            BcoRI

1921  CGAGATTTTA GACATTGCTA CCGATTTAGA AATCGTGAAA AAAAGTGGCT CTTGGTATTC TTATGCAGAT ACTAAACTAG
      >...................................recA.....................................>

2001  GACAAGGGCG AGATGCCGTG CGTGCGGTAT TGAAAGATAA TCCAGAATTA GCCGAAGAAT TAGAAGAGAA AATTAAAGAA
      >...................................recA.....................................>
              CGAGATCT>>.......OEF1.......>>
               ------
               BglII

2081  GAATTAGAGA AAAAATAGAT TTTTTAGTTT TTTTAATTAA ACGAAAAATC CGTTCACTTT GTTGAACGGA TTTTTTTATG
      >......recA......>>

2161  CTTGAATGAA TTTATTTCCA ATGGATTGAA TAGCCATGCA CTTTTAAATC TTCGCTATCA TAAGTGATTT CTTTGTCGGT

2241  GTTGGGATAG CAAACTTTAA GTCCTGCGTA TTTGGCAATG GCATGTCCTG CGGCAATGTC CCAAAAGTTT ACAGGTCTAA

2321  AGCGGGTGTA CTCCGTAGCC CACCGATCGG CAATTAGCCC AAGTTTGATA ACGCTTCCCA TAGGCTTTGT GCGGAAAATT

2401  TCATGTTCGG ATTTAATTTT TTTGATGTAT TCCTCGGTGC CAGGATCCAT GTGGAATTTG CTACAAAGAA AAGTGTAATC

2481  TTCGGGCAAA TCCATGGTAG GAATTGGCTT GCTGTGTTTC ATCAATTGTT CAAAAAAATC CGATTTCAGA GCCATTTTGT

2561  GCAATTGTTG TTGAGTCCCG ATGAATTTAC GAGAAGGGCA TTTATCGCTA CCGAAATAGA ACAATCCAAG CGATGGGGCG

2641  TACAAAACTC CTAGCTTAGC CGTATTATTC TCAACTAAGC CTAGACACAC GCAATATTCA TCTGTTTTGT TGACAAAATC

2721  CATGGTGCCA TCAATAGGGT CTGCAATCCA ATAGGTGGGC GTATTTCTAA TTTCTTGTAA AGAATCCTTA TCTCCTTCCT

2801  CACTAAAGTA TGGAATGTCT GTAAAGGAAA CATGTTTTTG CAAGATTTTG TTGGCGGCTA AATCTGCACT TGTAACAGGC

2881  GATCCGTCGG CTTTGGTCTC GGTGGAGAAT CCGTTTTGGA TTGTTTTAAA ACCTCTTCGC CAGCAAGTGC TACAGCCCGT

2961  GTTGCGATTT CTAATAAATT CATAATCATT CTTTTATTCT CGAACAAAGT CAAATAATTC TCTGTATTAA AAAATAATTT

3041  TGGCGATAAA AATTAAAATT TATATATAAA ATATCTCTGC AAAAAACCAA ATCAAATATT TAGTGAAATA AAAAAAATTA

3121  GATTGTAAAT TTGCCTTATG TTTTTAGAGA ATACCATAAA TCATAGAAAA AATACGGGCT GGATCGAAGT AATCTGTGGC

3201  TCTATGTTTT CGGGCAAAAC CGAAGAGTTG ATTCGTAGAG TGAAACGAGC CGAATTGGCT GGGCAAAAGG TAGAAATCTT
                                           <<..........R5...........<<AAGCTTAAG
                                                                      ------
                                                                     HindIII

3281  TAAACCCGCA ATTGATAAAC GCTACGATGA GCAAGATGTG GTATCGCATG ATGAAAACAA AAAACAAGCA ACCCCGATTG

3361  AGGCGAGTTC TAACTTGCCC ATTTTAGCAA GCGATTGTGA TGTGGTGGGG ATAGATGAGG CTCAATTCTT TGACGAAGGA

3441  ATTGTTGAGG TGGCAAATCT TTTAGCTAAT TCGGGGAAAA GAATAATTAT TGCGGGATTA GACATGGATT TTAAAGGTCG
                                                                <<.......RrecAOR1.......<<

3521  TCCATTTGGT CCTATGCCAA ATTTAATGGC GGTAGCGGAA TATGTGACCA AAGTGCATGC AATCTGTGTG AAAACAGGGA
```

Figure 2B continued table 5

| group | no. of chickens | Treatment | | | | Results | |
|---|---|---|---|---|---|---|---|
| | | vaccination at day 1 | | challenge at day 25 | challenge at day 31 | % of max airsac score at day 10 (safety) | % of max airsac score at day 38 (efficacy) |
| 1 | 25 | NDV | RecA aerosol | NDV | WT-OR aerosol | 2.5 | 25[b] |
| 2 | 25 | NDV | PurD aerosol | NDV | WT-OR aerosol | 7.5 | 23[b] |
| 3 | 25 | NDV | WT-OR aerosol | NDV | WT-OR aerosol | 68 | 10[b] |
| 4 | 25 | NDV | | NDV | WT-OR aerosol | 0 | 47 |
| 5 | 25 | NDV | | NDV | | 0 | 2 |

[b] Significantly different ($p<0.05$) compared to the controls (group 11) using two-sided Mann-Whitney U test

Figure 2B continued table 6

| group | no. of chickens | Treatment | | | | Results |
|---|---|---|---|---|---|---|
| | | vaccination at day 1 | | day 30 | challenge day 35 | % reduction |
| 1 | 15 | | PurD aerosol | NDV | WT-OR aerosol | no reduction |
| 2 | 15 | NDV | PurD aerosol | NDV | WT-OR aerosol | 54%[b] |
| 3 | 15 | NDV | | NDV | WT-OR aerosol | no reduction |
| 4 | 15 | MAS | | NDV | WT-OR aerosol | no reduction |
| 5 | 15 | MAS | PurD aerosol | NDV | VT-OR aerosol | 50%[b] |

[b] Significantly different ($p<0.05$) compared to the controls (group 11) using two-sided Mann-Whitney U test

SEQUENCE LISTING

<160> NUMBER OF SEQ ID NOS: 10

<210> SEQ ID NO 1
<211> LENGTH: 32
<212> TYPE: DNA
<213> ORGANISM: Artificial
<220> FEATURE:
<223> OTHER INFORMATION: Plasmid or primer

<400> SEQUENCE: 1
cttaagcttg gatccttgtg gcgtggcttt ag 32

<210> SEQ ID NO 2
<211> LENGTH: 33
<212> TYPE: DNA
<213> ORGANISM: Artificial
<220> FEATURE:
<223> OTHER INFORMATION: Plasmid or primer

<400> SEQUENCE: 2
cttaagcttc ccagccaatt cggctcgttt cac 33

<210> SEQ ID NO 3
<211> LENGTH: 28
<212> TYPE: DNA
<213> ORGANISM: Artificial
<220> FEATURE:
<223> OTHER INFORMATION: Plasmid or primer

<400> SEQUENCE: 3
cgagatctcg tgcgtgcggt attgaaag 28

<210> SEQ ID NO 4
<211> LENGTH: 44
<212> TYPE: DNA
<213> ORGANISM: Artificial
<220> FEATURE:
<223> OTHER INFORMATION: Plasmid or primer

<400> SEQUENCE: 4
accgcacgca cgagatctcg ggctttgtcg cccatcatca tcac 44

<210> SEQ ID NO 5
<211> LENGTH: 32
<212> TYPE: DNA
<213> ORGANISM: Artificial
<220> FEATURE:
<223> OTHER INFORMATION: Plasmid or primer

<400> SEQUENCE: 5

-continued cttaagcttg gagcgtgtag tgctcgccat cg 32

<210> SEQ ID NO 6
<211> LENGTH: 31
<212> TYPE: DNA
<213> ORGANISM: Artificial
<220> FEATURE:
<223> OTHER INFORMATION: Plasmid or primer

<400> SEQUENCE: 6
cttaagcttc agtggagcgg cagatacaga g 31

<210> SEQ ID NO 7
<211> LENGTH: 28
<212> TYPE: DNA
<213> ORGANISM: Artificial
<220> FEATURE:
<223> OTHER INFORMATION: Plasmid or primer

<400> SEQUENCE: 7
gagatctggc gctacgctag aagaagcc 28

<210> SEQ ID NO 8
<211> LENGTH: 46
<212> TYPE: DNA
<213> ORGANISM: Artificial
<220> FEATURE:
<223> OTHER INFORMATION: Plasmid or primer

<400> SEQUENCE: 8
cttctagcgt agcgccagat ctcatttgtt cggttccagc gtttcc 46

<210> SEQ ID NO 9
<211> LENGTH: 4278
<212> TYPE: DNA
<213> ORGANISM: Artificial
<220> FEATURE:
<223> OTHER INFORMATION: Plasmid or primer
<220> FEATURE:
<221> NAME/KEY: misc_feature
<222> LOCATION: (1309)..(1309)
<223> OTHER INFORMATION: n is a, c, g, or t
<220> FEATURE:
<221> NAME/KEY: misc_feature
<222> LOCATION: (2748)..(2748)
<223> OTHER INFORMATION: n is a, c, g, or t

<400> SEQUENCE: 9
gttcgaccaa acggcttgtt gtgcggtgaa acatagcact ccttgtggcg tggctttaga 60
tgatgatatt ttgcaagcgt cttaagcttg gaaccaaaaa gcacacgact gcgacccgat 120
ttcgattttt ggtggcattg taacttttaa taaaaaagta acaaaagcag tggcagaaaa 180
atgtaacgag attttccttg aaatcgttgc tgcaccgagc tttgagccag aggctttgga 240
agtttttgct aaaaagaaaa atttgcgcgt gattgaagtt aaaaatccat taagcgataa 300
aatgcaactc gtgcaagtag atggcggatt gctcgtgcaa gaaatcgaca aatcgtttag 360
caatgatttt aaagtagtaa ccgaaaaaca acctaccgaa aagcaacttt ctgatttgga 420
atttgccatg aaagtagtga aacatgtaaa gagcaatgcc atcgtggttg ccacaaacgg 480
acaagctcta ggcgtgggca caggcgagac taatcgtatt tgggcagcac agcaggcgat 540
tcagcgtgca aaggaaaaaa cacaagaaaa tctagttttg gcttccgatg ccttttttccc 600 attcagagat gtggtagatt atgcagcaca agaaggcatt acagccttga ttcacccagg 660
aggaagcatg cgcgaccaag agagcataga cgcggctaat gaacacggaa tcccgatgat 720

-continued

```
catcagcggt atgagacatt tcttacatta aatcaaaaaa tctaaacaat aattatcaat    780
aattctaaaa cacaataagt atgaatgcaa atgattacaa aaaaatactc atcgtaggaa    840
acggcgcaag agaacacgcc atcgggtgga aaattaaaca agaccaccct tcttgcgagc    900
ttttctttgc gccaggaaac gctggaaccg aacaaattgg aaaaaacatc gtagctgaat    960
ctaattatgg ctagatctgg cgctacgcta gaagtaatgc tttttgctca acaaaatgat   1020
atagacttaa cgattgtagg tccagaagca gaattggtag aaggtattgt agacttgttt   1080
gaatccaatc aattaagaat ttttggtcca gataagcgtg cggctaaatt ggaaggcagc   1140
aaggcttttg ccaaagattt tatggagaaa tacggcgtgc gcacggcttt tgccaaaagt   1200
ttcaacaatt ttgtagacgc tagagattat gtaaaagagc tcacgcaatt ccctatcgtg   1260
atcaaagcca gtggcttggc agcaggaaaa ggtgtgatca tcgtgcacnt acaacttgaa   1320
gccgaaacta ctttgcgcaa aatcatggaa gacaaaacct ttggcgaagc aggcaacgag   1380
gtcgtaatcg aggaatactt aaaaggtgtg gaagtttctg tgctttctat ctttaaccat   1440
aaagaaatta aaactttctt gcctgtaaaa gaccacaaga aaatcggaaa aggcgaaaca   1500
ggactcaaca cgggcggaat gggcgtagtg gctcctaacc cgcattttac cgatgagcac   1560
atgaaggagt ttgagaaaaa cattttgctc ccaacacaaa aagggctctt ggcagaaaaa   1620
atgcattttg caggcattat tttctttggg cttatgatta ccgagcatgg tatttatcta   1680
ttggaataca acatgcgatt tggcgaccca gaaaccgaag cacttttgcc tttgatggag   1740
aatgatttag tagccctcat cgattccgca atacaccagc aagacattga acttaaatgg   1800
aaaaacgaac atgcttgctg tgtagtaatg gcgagcggtg gctacccagg cacttacgaa   1860
actggttttg aaatccgagg attgaacaaa gttgatgttc ccgtatttat tgcaggagcc   1920
agagaagaaa gtggaaaaat ctacaccaca ggcgggcgcg tgctcaatgt ggtgggaact   1980
ggcgctacgc tagaagaagc cagaaaagtg gcttacgaaa atatccataa aatcgagatc   2040
tggaattttg attatgaata ttatcgcgaa gacatcggga agatataatc tcgctgattt   2100
ttaaccaaaa catatttaaa aacgcttttg ttacttttat aaacaaaggc gtttttctat   2160
ttttgtgcca ctataacatg atttaaccca tgaaaaaaat actaaaaata ctcatttttc   2220
tactgctcat tccttgggtt tatgccctga ttttaatctt tataaatcca cctatcacca   2280
ttacacagct gagcaattta tcttatggtt tctccagaac acagctcgct tatgatgaaa   2340
ttccggctag tgctaaatgg gctgtaattg cagcagaaga ccagaatttt gccattcata   2400
atggctttga ttttaaagaa attaaaaccg cctacgagaa aaacaaagcg ggcaagaaat   2460
tgcgtggcgg gagcaccctt tcgcaacaaa ctgccaaaaa tgtatttttg tggcaagggc   2520
gcacttggat tagaaaagga ttggaaacct actgcacctt tatcatcgaa acgctgtgga   2580
gcaaggagcg tattttgcaa gtttacctca acaatgccga aatgggcaaa ggcgtttatg   2640
gcatagaggc agcggcgcaa tattatttta agaaaaacgc ctcacagctc acgcctaccg   2700
agacggcacg catcattgcc tgcctgccca atcccaaaaa atacaatnta aacccgccaa   2760
gtgcctacat ctcaaaacgc ggacaatgga ttctgcgcca agtgcgaaac ttgaaaggcg   2820
atagggctct gagcgagatt gtgaacacgc cctaacgcct gcctcaactc tttgcacaca   2880
gtttaccaac tctctgcgaa gagttcacaa actcttcgca cacacttccc caagtctttg   2940
caaagagttg ggagatactt aggcacaaaa aaaaggaacc tcatgaatag aggttccctc   3000
ttccttaaaa ggaataaata ataatgtttt ttaagcttta ggcttggcta ctttttcaaa   3060
```

-continued

```
gcctgctgcc ttcatgctat ctaggatacg cttgcctggg cggtagttta cgcctacctt   3120

tttgattaag cccgaatgaa aatctttctc tgtatctgcc gctccactgc ttaaagtggc   3180

atagagcgag ccaagcttat ctaaacgaac gattttgccc gctgccaagg cgtcttgaat   3240

tacaagctta agattctcta gcgcaatgat aacgccacga atatctgcct cgctgagtgc   3300

cgaaaacttc tcgatttgct taacgagctg gtctatatcc atttctccat cgcttgccac   3360

cacggcatag tatttttgtg gctcccctgg cttgcttggg tttctacgct gaattacatt   3420

gtattttatg ctcataatta ctctattttt aatagcctcc cgatggatat aaagttacgc   3480

tacaattagg gtctccataa gcaaatctat acccctctct ttcatattcc cttctcattc   3540

ttcttgctcc atctctcaag gcatccgctc tattactgct atacccctcc tgaagaaatg   3600

tgtctgcact tgaagaagaa tatgaagagc tatgagaatc gtgcaacata gtccaagctc   3660

catcttgagc tataacattt gcatgacatg taacacctat agtataataa aatctcctag   3720

gaggttgtgt tccaccacca cctccagagc tactactttt tttacattgt ccattttggt   3780

tagcatgatt ttgtccgcca tcacttacta acttcttagc ttctgctaag gctttttctc   3840

ttgctttctt ttcagcatct gcttggctaa ttccactcac tgctgtagct gtcgcttctt   3900

ttttatagtt taccgaggtt ccataatagc cactactaca attgtttctt gtaaagtttt   3960

tattaaaaga ttgagtttgt gttgaggtgt accctccgaa acctttttact tctacagtaa   4020

aggtagaact ccccatgctt acggggaagg tggcgatagt atacgattgc cctgccggca   4080

tttgttttac ttgatacact ccatctcctc ccacttctat gcttgccgtt aaattaccac   4140

taccgctaaa agagccttct gctattttta gtgttaaatc atttatatcc cctccttgtc   4200

cttttgcaga agcttttgtt acacttacag catcataagc tccttttcca ttggtataag   4260

gtatttatat ggccaaac                                                 4278
```

<210> SEQ ID NO 10
<211> LENGTH: 3646
<212> TYPE: DNA
<213> ORGANISM: Artificial
<220> FEATURE:
<223> OTHER INFORMATION: Plasmid or primer

<400> SEQUENCE: 10

```
taaagctgta awtcgctata aacgcccttt aggataaaat ctgccatttt ttgcagtatt     60

ttwatagcta aaatttagaa aacaccatct cgagtaaagg agcgtgtagt gctcgccatc    120

gttgagcgat tgcccaccct caattgattt gggcgaatac cttaagcttt tgaaataaat    180

ggcatcttct agcgacacat tttgcgcaga aatcatgcaa aaagccccgc ataaaaagct    240

gaataaaaaw gctawtyttc ttgtttaaaa aaactcataa attcccccaa atatagaaat    300

attctgtgaa aagttgcaat ttattaacac tatgtgcttg cttttaatga aaaaagtaga    360

ttatttttcc gaatccgaaa gtttatttac gccccatccg atgcctagtc ccmscgatag    420

ccatgattaa tacaaataca attaaatcaw atttttcmcm twwaccatag cacaacactt    480

gctagctcaa cgagtactag agtggtaaaa aggatttttt gacgattatt catgatttta    540

tttttctcaa aggtaaatat tttaaaccat aatttcacaa atcttaaaat ctatttaaat    600

aatagagaaa ccagaaaaaa atcgtatttt tacggaatga ataaaatgtt acaagtaggc    660

gataaaatgc ccgatttcaa aggtgtagac caatttggga aggagcattc atctgccgat    720

ttcaaaaatc agaaattagt cgttttttttc tacccaaaag ccagtacgcc aggttgcacg    780

gcagaggctt gcaacatcaa cgataatctt gatgcgctaa aagcacaagg ctaccaagtg    840
```

-continued

```
ataggcgtga gtgcagattc ggtagaaaaa caacgaaaat tcagtgataa atacgatttt    900
aaattccctg tgattgccga tgtggataag aaaattattg aagcatttgg cgtgtggggc    960
gaaaagaaat tcatgggtaa aacctatgac ggaattcatc gtacgacatt cattattgat   1020
gaaaacggag tggtggagcg cgtgatagaa aaagtgaaaa caaaagatca taccaatcaa   1080
attttaaatt cagaaaaata aaaatatgag cgaaatagac gaagcgaaaa ggaaagcact   1140
ccagctagtg cttgataaaa tggacaaaag ctatggtaaa ggtgccgtga tgatgatggg   1200
cgacaaagcc atagacgaaa atattccagt aatccctacg ggtctctag gtttagattt   1260
agccttgggc gtgggagggt atccgcgcgc gagatctcgt gcgtgcggtg tagaatcgtg   1320
gagatttacg gtccagaatc ttctggtaaa accactttgg caattcatgc cattgccgaa   1380
gctcaaaagt ctggcggaat tgcagctttc atcgatgcag agcacgcatt tgatagatat   1440
tacgcagaaa aattaggcgt agatgttgag catttaatta tctctcagcc agataatggg   1500
gagcaagctt tagaaattgc cgataactta atccgttcag gtgcaattga tattattgta   1560
atcgattcgg tagcggcttt aacgccaaag tcggaaatcg acggagatat gggcgattcc   1620
aaaatgggat tgcaagcgcg tttgatgtct caagccttga gaaagctcac gggaactatc   1680
aataaaacca aatgtactgc tattttcatc aaccaattga gagagaaaat cggtgtgatg   1740
ttcggtagtc cagaaaccac aacgggtggt aatgcactta aattctatgc atcggtgcgt   1800
ctagacattc gtcgttctac tcagattaaa gatgggaacg atgtcatcgg aaacttgact   1860
cgcgtaaaag tagtgaaaaa caaagtagct ccgccattcc gtagtgcaga attcgacatt   1920
atgtatggcg aaggaatctc taaagcaggc gagattttag acattgctac cgatttagaa   1980
atcgtgaaaa aaagtggctc ttggtattct tatgcagata ctaaactagg acaagggcga   2040
gatgccgtgc gtgcggtatt gaaagataat ccagaattag ccgaagaatt agaagagaaa   2100
attaaagaac gagatctgaa ttagagaaaa aatagatttt ttagtttttt taattaaacg   2160
aaaaatccgt tcactttgtt gaacggattt ttttatgctt gaatgaattt atttccaatg   2220
gattgaatag ccatgcactt ttaaatcttc gctatcataa gtgatttctt tgtcggtgtt   2280
gggatagcaa actttaagtc ctgcgtattt ggcaatggca tgtcctgcgg caatgtccca   2340
aaagtttaca ggtctaaagc gggtgtactc cgtagcccac cgatcggcaa ttagcccaag   2400
tttgataacg cttcccatag gctttgtgcg gaaaatttca tgttcggatt taattttttt   2460
gatgtattcc tcggtgccag gatccatgtg gaatttgcta caaagaaaag tgtaatcttc   2520
gggcaaatcc atggtaggaa ttggcttgct gtgtttcatc aattgttcaa aaaaatccga   2580
tttcagagcc attttgtgca attgttgttg agtcccgatg aatttacgag aagggcattt   2640
atcgctaccg aaatagaaca atccaagcga tggggcgtac aaaactccta gcttagccgt   2700
attattctca actaagccta gacacacgca atattcatct gttttgttga caaaatccat   2760
ggtgccatca atagggtctg caatccaata ggtgggcgta tttctaattt cttgtaaaga   2820
atccttatct ccttcctcac taaagtatgg aatgtctgta aaggaaacat gtttttgcaa   2880
gattttgttg gcggctaaat ctgcacttgt aacaggcgat ccgtcggctt tggtctcggt   2940
ggagaatccg ttttggattg ttttaaaacc tcttcgccag caagtgctac agcccgtgtt   3000
gcgatttcta ataaattcat aatcattctt ttattctcga acaaagtcaa ataattctct   3060
gtattaaaaa ataattttgg cgataaaaat taaaatttat atataaaata tctctgcaaa   3120
aaaccaaatc aaatatttag tgaaataaaa aaaattagat tgtaaatttg ccttatgttt   3180
```

-continued

```
ttagagaata ccataaatca tagaaaaaat acgggctgga tcgaagtaat ctgtggctct   3240

atgttttcgg gcaaaaccga agagttgatt cgtagagtga aacgagccga attggctggg   3300

caaaaggtag aaatcttaag cttaagtaaa cccgcaattg ataaacgcta cgatgagcaa   3360

gatgtggtat cgcatgatga aaacaaaaaa caagcaaccc cgattgaggc gagttctaac   3420

ttgcccattt tagcaagcga ttgtgatgtg gtggggatag atgaggctca attctttgac   3480

gaaggaattg ttgaggtggc aaatctttta gctaattcgg ggaaaagaat aattattgcg   3540

ggattagaca tggattttaa aggtcgtcca tttggtccta tgccaaattt aatggcggta   3600

gcggaatatg tgaccaaagt gcatgcaatc tgtgtgaaaa caggga                  3646
```

COMBINATION VACCINE FOR POULTRY

The present invention relates to a combination vaccine for the protection of poultry against *Ornithobacterium rhinotracheale*, to the use of a live over-attenuated *Ornithobacterium rhinotracheale* strain and a live attenuated poultry virus for the manufacturing of such a combination vaccine, to methods for the preparation of said combination vaccine and to vaccination kits for the immunization of poultry against *Ornithobacterium rhinotracheale.*

Over the last decades, in many countries a strong raise in both the number of poultry farms, and in addition, an increasing number of animals per farm has been seen. This situation has a serious consequence: large scale outbreaks of poultry diseases are seen more and more frequently. This in turn has caused an increasing need for new and better vaccines and vaccination programs in these countries.

Nowadays, most animals are immunized against a number of diseases of viral, bacterial and parasitic origin. Examples of bacterial agents infective to poultry are *Ornithobacterium rhinotracheale, Haemophilus paragallinarum* (Coryza), *Salmonella* spp, *Pasteurella multocida, Bordetella bronchiseptica* and *E. coli*. Examples of viral poultry pathogens are Newcastle Disease virus (NDV), Infectious Bronchitis virus (IBV), Turkey Rhinotracheitis virus (TRT), Herpesvirus of Turkeys (HVT), Fowlpox virus (FPV), Avian Reovirus (ARV), Infectious Laryngotracheitis virus (ILT), Marek's Disease Virus (MDV) and Infectious Bursal Disease virus (IBDV).

*Ornithobacterium rhinotracheale* is a relatively new bacterium causing a disease known for about a decade now, and found frequently in, inter alia, chickens and turkeys. Clinical signs in chickens are e.g. airsacculitis or coughing, pneumonic lungs or pleuritis. In turkey flocks in several parts of the world, a comparable infection of the respiratory tract is found. Mortality in flocks suffering from the disease can be as high as 5%. The first clinical signs are comparable to infection in chicken: sneezing and nasal discharge. In some animals clinical signs of acute infection are seen. Examination of sacrificed animals shows edema of the lungs, fibrinopurulent pneumonia and often serofibrinous pericarditis and serofibrinous infection of the airsacs. *Ornithobacterium rhinotracheale* is extensively described in European Patent EP0.625.190. Identification, serotyping and experimental infection in turkeys and chickens have been described e.g. by van Empel, P.C.M. et al., in Journ. of Clin. Microbiol. 35: 418-421 (1997), by van Empel, P.C.M. et al., in Avian Diseases 40: 858-864 (1996) and by van Empel, P.C.M. et al., in Avian Pathology 28:217-227 (1999). A review on *Ornithobacterium rhinotracheale* has been published in Avian Pathology 28: 217-227 (1999) by van Empel, P.C.M. and Hafez, H.M.

If an animal suffers from infection with a virulent pathogen, the immune system will try to remove the pathogen. Provided that the infected animal survives the infection, it usually develops a long-lasting immunity against the pathogen.

Vaccination with an attenuated pathogen mimics the natural infection in that it induces immunity, however without causing unacceptable clinical signs. Some clinical signs, in other words; some residual virulence, has to be accepted however because without this, the immune system will in most cases be insufficiently triggered. Generally spoken, vaccination is the way to avoid large scale infection and its negative consequences.

Vaccines against most of the known pathogenic bacteria and pathogenic viruses may comprise either inactivated or live attenuated pathogens, depending upon the purpose and the way of administration. But if it comes to efficient and early protection of young animals, combined with ease of application, live attenuated vaccines are clearly an attractive choice. Such vaccines can be given from the day of birth, for poultry even in ovo, and if preferred, they can be applied from day of birth simply by spraying or through drinking-water application.

Spraying of vaccines is especially attractive for poultry and is currently applied on a very large scale for e.g.: Infectious Bronchitis virus, Newcastle Disease virus, Turkey Rhinotracheitis virus, Infectious Bursal Disease virus and Avian Reovirus.

The main disadvantage of vaccines derived from virulent pathogens is, that they must be carefully and sufficiently attenuated in order to be safe.

This requirement can relatively easy be fulfilled for highly virulent microorganisms, because they can in most cases be highly attenuated while retaining their vaccinating (immunity-inducing) capacities.

Of the bacteria mentioned above, *Ornithobacterium rhinotracheale* belongs to the so-called secondary pathogens. A secondary pathogenic bacterium is a bacterium that does not readily cause disease in healthy animals. As a consequence, the immune system will not or insufficiently be triggered and therefore, no immunity will develop. In animals kept under sub-optimal conditions such as high stock density and stress, such secondary pathogenic bacteria can however cause dramatic morbidity and mortality. Thus, for secondary pathogens, the design of a live attenuated vaccine is severely hampered by the unpredictable behavior of the bacteria. Unpredictable in the sense that the level of virulence of such bacteria does not solely depend on their level of attenuation, but (contrary to what is the case for primary pathogens) also largely on the physical situation of the animal to be vaccinated.

This is a real dilemma as will be sketched below using *Ornithobacterium rhinotracheale* as example.

*Ornithobacterium rhinotracheale* is a relatively mild bacterium, in the sense that in perfectly healthy Specified Pathogen Free (SPF) poultry kept under optimal conditions it might be difficult to induce disease at all, even when using non-attenuated, wild-type, bacteria. Thus, such poultry, be it chickens, turkeys or ducks, even when "vaccinated" with the wild-type bacterium, are not affected and as a consequence they do not build up any protection against *Ornithobacterium rhinotracheale*. An example of a wild-type strain is the *Ornithobacterium rhinotracheale* strain 3263/91 as deposited at the Centraalbureau voor Schimmelcultures (CBS), Oosterstraat 1, PO. box 273, 3740 A G Baarn, The Netherlands, under accession-number 400.92.

However, poultry kept under standard conditions for commercial breeding, i.e. a high stock density, stress, poor ventilation and/or high ammonia levels, are much more vulnerable to *Ornithobacterium rhinotracheale*. They are severely affected by wild-type *Ornithobacterium rhinotracheale* strains.

Especially if such animals would already suffer from another infection the effect could be dramatic. In animals suffering from (sometimes even subclinical) infections with other bacteria or viruses, the wild-type bacterium often causes massive and severe morbidity.

In addition to this and unlike other secondary pathogenic bacteria, the pathological effects of any *Ornithobacterium rhinotracheale* strain in poultry not only depend on the virulence of the strain as such and the physical condition of the infected animal but, especially in the case of chickens, also heavily upon the chicken species. It is e.g. well-known in the art, that broilers are much more susceptible to *Ornithobacterium rhinotracheale* infection than layers.

For the reasons given above, the development of a live attenuated vaccine starting from a secondary pathogen in general and especially *Ornithobacterium rhinotracheale*, although possible, is complex to say the least. On the one hand, even a wild-type strain of these bacteria is not capable of inducing protection in perfectly healthy, less susceptible animals, whereas on the other hand even an attenuated strain is only suitable in some cases for use in susceptible animals or animals suffering from stress and other negative environmental factors, the suitability highly depending upon the level of stress and the poultry species.

Only a live over-attenuated *Ornithobacterium rhinotracheale* strain would be safe under all circumstances in poultry industry and in both broiler chickens and layer chickens. An attenuated strain, let alone an over-attenuated strain, will however not trigger any immune reaction in healthy, less susceptible animals, because in such animals even the virulent strain does not trigger an immune reaction.

This dilemma makes it difficult to provide vaccines based upon live secondary pathogens, more specifically *Ornithobacterium rhinotracheale*, that are both efficacious and safe, regardless the kind of animal to be vaccinated and its physical condition.

It is an objective of the present invention to provide vaccines that add to solving this dilemma.

In order to reach this goal, the present invention provides a combination vaccine for the protection of poultry against *Ornithobacterium rhinotracheale* wherein the combination vaccine comprises a live over-attenuated *Ornithobacterium rhinotracheale* strain and a live attenuated poultry virus.

The present invention relates to the surprising finding that even over-attenuated secondary pathogenic *Ornithobacterium rhinotracheale* bacteria are well capable of inducing a protective response provided that they are given in combination with a live attenuated poultry virus. Such over-attenuated secondary pathogenic bacteria are inherently safe because they only cause moderate clinical signs even when they would accidentally be administered at a moment in time at which a field infection with a wild-type virus has occurred.

An over-attenuated *Ornithobacterium rhinotracheale* bacterium is a bacterium that (contrary to an attenuated *Ornithobacterium rhinotracheale* strain) is not capable of inducing a protective immune response to *Ornithobacterium rhinotracheale* in primed animals. A primed animal is an animal that has received, prior to administration of the vaccine, a virulent pathogen that predisposes for infection with a secondary pathogenic bacterium. Primed animals provide an objective animal model for testing the level of attenuation. Animals randomly taken from commercial farms would not provide a stable model, because inherently, their physical condition is difficult to establish and highly variable. Primed animals, contrary to this, are of known SPF-origin, they are by definition in good health and they received, as a priming, a well-defined amount of a well-defined pathogen. The priming virus of choice for the chicken model is Newcastle Disease virus. Turkey Rhinotracheitis virus is the priming virus of choice in turkeys. Thus, in order to see if an attenuated *Ornithobacterium rhinotracheale* bacterium for use in chickens indeed behaves over-attenuated in chickens, this should be tested in chickens primed with Newcastle disease virus, as is e.g. indicated in the Examples section.

A protective immune response is an immune response that gives, after challenge, a statistically significant decrease in respiratory tract lesion score of equal or more than 50% compared to non-vaccinated animals. The respiratory tract lesion score test is explained in the Examples section.

The nature of the mutation(s) leading to the over-attenuated behavior is not critical. Many attenuating mutations known in the art are suitable. Suitable *Ornithobacterium rhinotracheale* mutations are e.g. the classical PurD-, RecA- and Aro-mutations, known in the art for many bacterial species. Also, many temperature-sensitive mutants are suitable. Of these, PurD- and RecA-mutations are preferred. The PurD gene encodes a protein that is involved in the Purine ribonucleotide biosynthesis. A PurD-mutation is defined as a mutation that disturbs the Purine ribonucleotide biosynthesis in the sense that such a mutant makes less or less active or no PurD gene product compared to wild type *Ornithobacterium rhinotracheale* strains. The RecA gene encodes a protein that is involved in recombination processes. A RecA-mutation is defined as a mutation that disturbs recombination processes in the sense that such a mutant makes less or less active or no RecA gene product compared to wild type *Ornithobacterium rhinotracheale* strains.

Mutations such as PurD- and RecA-mutations are most easily obtained by simply deleting the gene encoding PurD and RecA. Such (site-directed) mutation techniques are well-known in the art.

The level of attenuation of the live attenuated viral component of the combination vaccine according to the invention is not critical. Usually, a live attenuated viral vaccine strain will be chosen that is suitable as a vaccine, i.e. a strain that induces protection against infection without causing an unacceptable level of pathogenicity. Many live attenuated viral poultry vaccines are commercially available. Such strains can simply be purchased from various producers.

Suitable live attenuated poultry viruses are e.g. Infectious Bronchitis virus, Turkey Rhinotracheitis virus, Newcastle Disease virus, Avian Reovirus and Marek's virus.

Examples of suitable live attenuated viral vaccine strains especially suitable in chickens are e.g. Nobilis IB 4/91, D1466, D274, H120, H52 and MA5 (IBV), Nobilis ILT (ILT), Nobilis Marek THV, Rismavac, SB1 and Marexine CA126 (MDV) and Nobilis ND Broiler, Clone 30, Hitchner, LaSota, Nobilis NDC2/Nobilis Newhatch C2 and Nobilis MA5. Such vaccines are available from Intervet International B.V., Wim de Korverstraat 35, 5831 A N Boxmeer, The Netherlands.

Nobilis Duck Plague is especially suitable for use in combination vaccines for ducks.

Nobilis TRT is especially suitable for use in combination vaccines for turkeys.

Preferably, the viral component of the combination vaccine is administered via the same route as the live over-attenuated *Ornithobacterium rhinotracheale* vaccine. *Ornithobacterium rhinotracheale* causes respiratory disease and sometimes severe inflammation reactions in the joints. These inflammation reactions are often seen when *Ornithobacterium rhinotracheale* enters the blood stream. Therefore, a suitable route of administration especially for combating inflammation reactions in the joints is subcutaneous or intramuscular injection of both the bacterial component and a live attenuated poultry virus causing systemic reactions. Examples of viruses, preferred for administration in the combination vaccine according to the invention are live attenuated Avian Reovirus, preferably Nobilis Reo 1133 and 2177, and Marek's virus.

*Ornithobacterium rhinotracheale* being a mainly respiratory disease, a preferred route however would be oral/nostril/respiratory tract vaccination. A more preferred route of vaccination would be vaccination by spray/aerosol, since in that case, the combined components would most directly reach the respiratory tract and other spots where immunity is most needed.

The preferred live attenuated viral components for oral-nostril- or respiratory tract application are those viruses known to cause respiratory disease, specifically Infectious Bronchitis virus, Turkey Rhinotracheitis virus and Newcastle Disease virus.

Of these, Nobilis TRT, Nobilis NDC2/Nobilis Newhatch C2 and Nobilis MA5 are the most preferred.

Although preferred, both the active components of the combination vaccine do not necessarily have to be administered in a mixed form. The way of administration for each component may depend on the specific properties of each of the components. For example, although administration by injection of such vaccines is also contemplated, the live over-attenuated *Ornithobacterium rhinotracheale* vaccine strains are preferably administered by the inexpensive mass application techniques commonly used for vaccination and well-known in the art, such as spraying/aerosol or drinking water application. It is very well possible that the viral component is preferably given through another route, e.g through parenteral administration.

Also other routes of administration are contemplated such as in ovo vaccination, of course with the proviso that the specific active component is able to evoke a protective immune response after administration.

Also, if both the bacterial and the viral component of a certain combination vaccine according to the invention would preferably be administered by spraying, this would not necessarily mean that they are both sprayed through the same nozzle. It could well be possible that, due to differences in viscosity of both the bacterial and viral component, the carriers and/or any excipients, both vaccine components are preferably sprayed through different nozzles. Nevertheless, this would of course still lead to the beneficial and synergistic effect that both the viral and the bacterial component of the combination vaccine have: after all, they would both reach the respiratory tract and exert their joined beneficial effect. Thus, it goes without saying that such separate administration of both components still gives the surprising effect and therefore is within the scope of the invention.

The present invention relies upon the fact that the live attenuated viral component triggers the animal in such a way that the over-attenuated *Ornithobacterium rhinotracheale* vaccine strain stays longer in the respiratory tract and more severely attacks the system. In pathogen-free hosts, the bacterium will disappear within one or two days. Most live attenuated poultry viruses (e.g. vaccine viruses) stay in the respiratory tract for up to a week at least. Therefore, the advantages of the present invention can also be achieved if the components of the combined vaccine are administered to the birds separated by a small interval of time. The unexpected synergetic effect as described in the present invention will e.g. readily be obtained if the live attenuated viral component is given in the period between seven days before, and two days after the live over-attenuated *Ornithobacterium rhinotracheale* vaccine strain is given.

Therefore, combination vaccines of live over-attenuated *Ornithobacterium rhinotracheale* and a live attenuated poultry virus as described in the present invention include those combinations in which the live attenuated viral component is given in the period between seven days before, and two days after the live over-attenuated *Ornithobacterium rhinotracheale* vaccine strain is given, and include those combinations in which the live attenuated viral component and the live over-attenuated *Ornithobacterium rhinotracheale* component are administered at different sites.

Merely as an additional example: the advantageous effect of the combination vaccine can also be obtained if one of the components, e.g. the live attenuated poultry virus is administered in ovo shortly before hatching, i.e. in the last quarter, preferably at day 18, and the live over-attenuated *Ornithobacterium rhinotracheale* vaccine strain is administered 0-7 days after hatching by e.g. spraying. Preferably, the amount of time between both vaccinations preferably does not exceed 7 days.

Preferably, the vaccination with the combi-vaccine is at one day of age. In a more preferred form of this embodiment, the live attenuated poultry virus and the live over-attenuated *Ornithobacterium rhinotracheale* vaccine strain are administered at the same time, if only for ease of application. In an even more preferred form, the live attenuated poultry virus and the live over-attenuated *Ornithobacterium rhinotracheale* vaccine strain are administered by means of spraying.

Spraying can be done through a course spray giving visible droplets, or through the use of a nozzle that provides a fine mist. The latter has the advantage that the vaccine more efficiently reaches the lower parts of the respiratory tract.

The vaccine according to the invention comprises an effective dosage of the active components, i.e. an amount of immunizing active component that will induce protective immunity in the vaccinated birds against challenge with *Ornithobacterium rhinotracheale* and preferably to the live attenuated viral component of the combination vaccine. (Induction of a protective immunity in the vaccinated birds against the viral component of the combination vaccine is of course desirable, but not in principle necessary).

As mentioned above, a protective immune response is an immune response that gives, after challenge, a (statistically significant) decrease in respiratory tract lesion score of equal or more than 50% compared to non-vaccinated animals. In poultry, a higher level of protection against *Ornithobacterium rhinotracheale* would e.g. follow directly from a comparison of lesion scores of vaccinated versus non-vaccinated animals after challenge.

The *Ornithobacterium rhinotracheale* component can in principle be administered in a suitable dose of between $10^3$ and $10^{10}$ colony forming units.

Typically, the *Ornithobacterium rhinotracheale* component will be administered in a dose of between $10^5$ and $10^8$ colony forming units.

The live attenuated poultry virus component will usually be given also in a dose of between $10^3$ $TCID_{50}$ and $10^7$ $TCID_{50}$, although this might of course strongly depend upon the amount of viruses prescribed by the manufacturer of the live attenuated viral component.

The combination vaccine can be used as a primary vaccination, if desired followed by one or more booster vaccinations. The combined vaccine is also suited for incorporation in vaccination programs that also involve the use of other vaccines in a live or inactivated form. Merely as an example, broilers may be vaccinated at one day of age followed by a booster immunization at 10-21 days. Laying stock or reproduction stock may be vaccinated at 1-10 days followed by booster vaccinations at 26-38 days and 16-20 weeks.

In a more preferred form, the combination vaccine comprises a combination of an over-attenuated *Ornithobacterium rhinotracheale* and Newcastle Disease virus, even more preferably NCD Clone 30, obtainable from Intervet International B.V., Wim de Korverstraat 35, 5831 AN Boxmeer, The Netherlands.

In an still even more preferred form, the combination vaccine comprises a combination of an over-attenuated *Ornithobacterium rhinotracheale* and Newcastle Disease virus NDC2, as deposited at the CNCM of the Institut Pasteur, 25 Rue du Docteur Roux, Paris, France under Accession number I-1614.

In another more preferred form, the combination vaccine comprises a combination of an over-attenuated *Ornithobacterium rhinotracheale* and a live attenuated Turkey Rhinotracheitis virus, even more preferably Nobilis TRT, obtainable from Intervet International B.V., Wim de Korverstraat 35, 5831 A N Boxmeer, The Netherlands.

In again another more preferred form, the combination vaccine comprises a combination of an over-attenuated *Ornithobacterium rhinotracheale* and a live attenuated Infectious Bronchitis virus, even more preferably Nobilis MA5, obtainable from Intervet International B.V., Wim de Korverstraat 35, 5831 A N Boxmeer, The Netherlands.

In still another more preferred form, the combination vaccine comprises a combination of an over-attenuated *Ornithobacterium rhinotracheale* and a live attenuated Avian Reovirus, even more preferably Nobilis Reo 1133 or 2177, obtainable from Intervet International B.V., Wim de Korverstraat 35, 5831 A N Boxmeer, The Netherlands.

The invention also relates to combination vaccines comprising, in addition to the two active components defined above, one or more additional antigens derived from a virus or micro-organism pathogenic to poultry or genetic information encoding said antigen.

More preferably, the virus or micro-organism is selected from the group consisting of Infectious Bronchitis virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitisvirus, Duck Plague virus, Egg Drop syndrome virus, Infectious Laryngotracheitis virus, Herpes Virus of Turkeys, Eimeria species, *Ornithobacterium rhinotracheale, Pasteurella multocida, Mycoplasma synoviae, Salmonella* species and *E. coli.*

The vaccine according to the invention can be prepared and marketed in the form of a suspension, or in a lyophilized form and additionally contains a pharmaceutically acceptable carrier customarily used for such active components. Carriers include stabilisers, diluents, preservatives and buffers.

Suitable stabilisers are for example SPGA, carbohydrates (such as dried milk, serum albumin or casein) or degradation products thereof. Suitable buffers are for example alkali metal phosphates. Suitable preservatives are thimerosal, merthiolate and gentamicin. Diluents include water, aqueous buffers (such as buffered saline), alcohols and polyols (such as glycerol).

If desired, the vaccine according to the invention may contain an adjuvant. Suitable compounds or compositions for this purpose include alum hydroxide, -phosphate, or -oxide, oil-in-water or water-in-oil emulsions based upon for example mineral oil, such as Bayol F® or Marcol 52® or a vegetable oil such as vitamin E acetate, and saponins.

Preferably, both the bacterial and the viral component of the combination vaccine according to the invention are packaged in a mixed form in the same container. They could be freeze-dried or stored at low temperature thereafter.

The present invention also contemplates a kit format which comprises a packaged multi-container unit having containers each comprising one of the active components as defined above. The kit may additionally comprise a container with a carrier for one or both of the active components, in which case the carrier preferably comprises an adjuvant. Such a kit is e.g. advantageous in case the active components are preferably not freeze-dried or premixed together, or when the active components are preferably administrated separated in place and/or time.

The active components of the kit according to the invention, i.e. the live over-attenuated *Ornithobacterium rhinotracheale* strain and the live attenuated poultry virus, and possibly a third and further active components, can be mixed prior to vaccination, or administered separately, at different administration sites and/or different moments of administration with the proviso's indicated above.

Still another embodiment of the present invention relates to the use of a live over-attenuated *Ornithobacterium rhinotracheale* strain and a live attenuated poultry virus for the manufacturing of a combination vaccine for the protection of poultry against *Ornithobacterium rhinotracheale.*

Also, another embodiment relates to the use of a live over-attenuated *Ornithobacterium rhinotracheale* strain and a live attenuated poultry virus for the manufacturing of a combination vaccine for the protection of poultry against *Ornithobacterium rhinotracheale*, wherein the live over-attenuated *Ornithobacterium rhinotracheale* strain and the live attenuated poultry virus are administered simultaneously, separately or sequentially. Simultaneous administration is administration of the live over-attenuated *Ornithobacterium rhinotracheale* strain and the live attenuated poultry virus at the same moment in time, preferably injected as a mixture, sprayed as a mixture sprayed from one nozzle or given as a mixture in the drinking water. Separate administration is administration of the live over-attenuated *Ornithobacterium rhinotracheale* strain and the live attenuated poultry virus from two different injection sites or, when sprayed, e.g. from two different nozzles, preferably at the same moment in time. Sequential administration is administration during which the live over-attenuated *Ornithobacterium rhinotracheale* strain and the live attenuated poultry virus are administered at different moments in time. The conditions for the various moments of administration are discussed above.

Again another embodiment of the present invention relates to methods for the preparation of a combination vaccine for the protection of poultry against *Ornithobacterium rhinotracheale.* Such methods comprise the admixing of a live over-attenuated *Ornithobacterium rhinotracheale* strain, a live attenuated poultry virus and a pharmaceutically acceptable carrier.

Such methods may also and/or alternatively comprise the packaging of a live over-attenuated *Ornithobacterium rhinotracheale* and a live attenuated poultry virus in separate containers that form part of a kit.

EXAMPLES

Example 1

Preparation of Live Over-attenuated *Ornithobacterium rhinotracheale* Strains.

Two commonly known attenuation targets, viz. purD and recA, were selected to create mutants.

Since serotype A strains are the most predominant and is also known to provide cross-protection against infections with other serotypes, this serotype was used to create the mutants.

Bacterial Strains and Plasmids *Escherichia coli* host strains TOP10 and TOP10F' were purchased from Invitrogen (Carlsbad, Calif.). pUC19 was derived from Clontech laboratories (Palo Alto, Calif.).

An *Ornithobacterium rhinotracheale* strain serotype A (OR-7 (095264 95.2932) Van Empel, P. C. M.; Molecular identification of *Ornithobacterium rhinotracheale;* (1998) ISBN 90-393-15744. Page 45.) was used as host strain for electroporation and homologous recombination. Chromosomal DNA of *Ornithobacterium rhinotracheale* strain 3263/91 (see above) was used as PCR template for making deletion constructs.

Culture Media, Buffers and Antibiotics

Luria-Bertani (LB) broth and terrific broth (TB, Sambrook, J., E. F. Fritsch, and T. Maniatis. Molecular cloning: a laboratory manual. (1989) Cold Spring Harbor Laboratory, Cold Spring Harbor, N.Y.) were used for liquid growth of bacterial *Escherichia coli* strains. For *Ornithobacterium rhinotracheale* (OR) Todd Hewitt (Becton Dickinson, Franklin Lakes, N.J., non irradiated) was used. For OR on plates, blood agar or Todd Hewitt agar supplemented with 4% sheep blood was used. LB agar plates were poured from melted LB-agar, which was cooled to 45° C. and then the appropriate antibiotics were added.

Oligonucleotides

All oligonucleotides were obtained from Life Technologies™ Gibco BRL (Paisley, UK) and are indicated in Table 1. Their location in the sequence is shown in FIGS. 2A and B.

PCR Amplification

PCR amplification was performed where the PCR mixture for cloning the recA and purD genes consisted of 40 U/ml of SuperTaq plus; 1×SuperTaq PCR buffer; 80 μM (each) of dATP, dCTP, dGTP and dTTP (HT BioTechnology Ltd., Cambridge, UK); 0.4 μM of both oligonucleotides and 1 μl of chromosomal DNA as template. Samples were analyzed on an agarose gel. For the overlap extension PCR (OE-PCR) the first PCR products were diluted a hundred fold and mixed 1:1. Then PCR was performed with the outer primers as described below.

The colony PCR method was performed as follows: part of the colony was picked from an agar plate and transferred into a PCR tube. The PCR mixture was added, containing: 10 U/ml of SuperTaq DNA polymerase; 1×SuperTaq PCR buffer; 80 μM (each) of dATP, dCTP, dGTP and dTTP (HT BioTechnology Ltd., Cambridge, UK) and 0.4 μM of both oligonucleotides. Samples were analyzed on an agarose gel.

TABLE 1

Oligonucleotides (primers) used for preparation of insertion-deletion constructs.

| Primer Name | Sequence (5'→3') | Features |
|---|---|---|
| PurD-F13 | CTTAAGCTTGGATCCTTGTGGCGTGGCTTTAG [SEQ ID NO.: 1] | HindIII site (underlined) |
| PurD-OE-R | *CTTCTAGCGTAGCGCCAGATCTC*ATTTGTTGGGTTCCAGCGTTTCC[SEQ ID NO.: 8] | BglII site (underlined) and overlap with PurD-OE-F (italics) |
| PurD-OE-F | *GAGATCTGGCGCTACGCTAGAAG*AAGCC [SEQ ID NO.: 7] | BglII site (underlined) and overlap with PurD-OE-R (italics) |
| PurD-R8 | CTTAAGCTTCAGTGGAGCGGCAGATACAGAG [SEQ ID NO.: 6] | HindIII site (underlined) |
| RecA-F6 | CTTAAGCTTGGAGCGTGTAGTGCTCGCCATCG [SEQ ID NO.: 5] | HindIII site (underlined) |
| recA-OE-R | *ACCGCACGCACGAGATCTCG*GGCTTTGTCGCCCATCATCATCAC[SEQ ID NO.: 4] | BglII site (underlined) and overlap with recA-OE-F (italics) |
| recA-OE-F | *CGAGATCTCGTGCGTGCGGT*ATTGAAAG [SEQ ID NO.: 3] | BglII site (underlined) and overlap with recA-OE-R (italics) |
| RecA-R5 | CTTAAGCTTCCCAGCCAATTCGGCTCGTTTCAC [SEQ ID NO.: 2] | HindIII site (underlined) |

Nucleotide Sequence Analysis

The nucleotide sequences of the purD and recA genes and their surroundings were determined. Sequencing was performed using a cycle sequencing protocol on a Perkin Elmer 9700 DNA thermal cycler with big dye terminators: approx. 50 ng of PCR product, 2 μl terminator ready reaction mix (Perkin Ehmer, Calif.) 2.4 pmoles of primer, 6 μl of buffer (200 mM Tris-HCl pH8.5; 5 mM $MgCl_2$) and aqua dest in a total of 20 μl.

DNA Manipulations

For sequencing, the purD and recA genes and their flanking regions were amplified by PCR and cloned into a general purpose cloning vector.

Electroporation of *Ornithobacterium rhinotracheale.*

*Ornithobacterium rhinotracheale* was made electro-competent by growing in Todd-Hewitt broth until an OD 600 nm of 0.3. During further manipulations, the cells were kept on ice. The culture was washed twice with ice-cold water and once with ice cold 10% glycerol. This suspension was centrifuged again and the cells were resuspended in 0.5 ml of 10% glycerol and stored on ice until use.

Electroporation was performed using a BTX ECM630 Genepulser (San Diego, Calif). 1-2 μg of plasmid DNA was mixed with 50 μl of electro competent *Ornithobacterium rhinotracheale* cells in a 2 mm cuvette. A pulse of 20-24 msec. was delivered using 2500V; HV capacity; 25 μF and 800 Ω. After electroporation, 1 ml of TH broth was added and the cells were recovered for 2 hours at 37° C. and 100 RPM. Viability was checked on blood agar plates. Antibiotic resistant colonies were selected on TH agar with 4% blood and antibiotic at a selective concentration.

UV-sensitivity of recA Recombinants.

In order to check a recombination in the recA gene, its sensitivity to UV was tested. Bacteria were plated onto blood agar and UV irradiated with a wavelength of 365 nm at a distance of about 10 cm. Different exposure times were tested, ranging from 0 to 120 seconds. Plates were then incubated and growth of recA-mutant colonies were compared to growth of purD-mutant colonies and colonies of the wild type strain.

Results

Sequencing recA and purD.

To obtain the sequence of the purD and recA genes of OR, degenerate primers were developed based on conserved regions of the genes derived from closely related bacteria. By means of genome walking, the flanking regions were determined. The complete sequences and the relevant features are shown in FIG. 2A for purD and FIG. 2B for recA.

Construction of the recA and purD Deletion and Insertion-deletion Constructs.

The strategy for construction an insertion-deletion mutant is depicted in FIG. 1. For the purD mutant the procedure was as follows. First, PCR on genomic *Ornithobacterium rhinotracheale* DNA was performed using 2 primer sets purD-F13 (+HindIII site) with purD-OE-R (upstream purD) and purD-OE-F with purD-R8 (+HindIII site) (downstream purD) to amplify the flanking regions of the purD gene. Overlap-extension PCR was performed with the purD-F13 and the purD-R8 primers using both purD PCR fragments as templates since the OE-R and OE-F primers overlap. This results in PCR fragments that contain both flanking regions of the purD gene and therefore the biggest part of the purD gene is deleted. These fragments were digested with HindIII and cloned into pUC19. Then an antibiotic resistance marker present on a 1.2 kb BamHI fragment was introduced in the BglII site that was included in the overlap sequence of the OE-F and OE-R primers.

A similar approach was followed for construction of the recA insertion-deletion construct. Primers recA-F6 and recA-OE-R (upstream recA), and recA-OE-F and recA-RS (downstream recA) were used in PCR for the flanking regions of the recA gene. OE-R and OE-F primers overlap and have an additional BglII site for insertion of the antibiotic resistance marker. The constructs were verified, plasmid DNA was isolated and used to electroporate *Ornithobacterium rhinotracheale.*

Verification of the Mutation in Recombinants.

After electroporation, colonies were obtained for both the recA and purD constructs, that showed antibiotic-resistance. Mutants for both genes were confirmed by PCR. The recA mutant clones were additionally confirmed by testing for their sensitivity to UV irradiation; the purD mutants and the parent strain were able to survive UV exposure times for more than 40 sec whereas the recA mutant died after 10 sec of irradiation.

Example 2

Comparison of Induction of Protection of Over-attenuated *Ornithobacterium rhinotracheale* Strains

TABLE 2 comparison of level of protection of over-attenuated mutants. Vaccine strains were applied by spraying. Each group consisted of 15 chickens. Challenge was done with wild-type. Respiratory scores are given as a percentage of the maximally possible score of the challenged group.

| Vacc. 2 weeks $2 * 10^7$ CFU/ml | Prim. Day 23 | Chall. Day 28 $3 * 10^8$ CFU | Resp. score. |
|---|---|---|---|
| O.r. RecA | NDV | 100 ml spray | 46 |
| O.r. PurD | NDV | 100 ml spray | 35 |
| — | NDV | 100 ml spray | 51 |

The affected organs of the birds were scored in a numerical scoring system:

Thoracic air sacs (TAS): 0=no abnormalities, 1=one air sac seriously affected by fibrinous airsacculitis or limited pinhead-sized foci of fibrinous exudate in both air sacs, 2=both air sacs seriously affected by fibrinous airsacculitis.

Abdominal air sacs (AAS): 0=no abnormalities, 1=pinhead-sized foci of fibrinous exudate or slight diffuse airsacculitis, 2=severe fibrinous airsacculitis.

Pneumonia: 0=no abnormalities, 1=unilateral pneumonia, 2=bilateral pneumonia.

Trachea: 0=no abnormalities, 1=some exudate in the tracheal lumen, 2=lumen of trachea filled with exudate.

Table 2 shows the result of a vaccination experiment in which two weeks old chickens were vaccinated by spray-vaccination of $2*10^7$ CFU in 100 ml spray solution of a RecA-mutant and a PurD-mutant of *Ornithobacterium rhinotracheale*. Priming was done with an NDV Lasota vaccine strain at day 23, and challenge with a wild-type *Ornithobacterium rhinotracheale* strain was done at day 28. The level of protection was determined by counting the trachea and lung lesions.

The figures of the respiratory lesion score (see column resp. score in Table 2) are to be interpreted as follows: the maximal possible lesion score is taken as 100% score. Non-vaccinated animals show a lesion score of 51%, and "vaccinated" animals have a lesion score of 46% (RecA) or 35% (PurD). This means that "vaccination" with RecA or PurD gives a level of protection of 8% (100%-(46*100%/51)) or 30% respectively.

A protective immune response, as defined above, is an immune response that gives, after challenge, a (statistically significant) decrease in respiratory tract lesion score of equal or more than 50% compared to non-vaccinated animals.

It follows from Table 2 that the respiratory lesion score of the groups that received vaccination with a mutant of *Ornithobacterium rhinotracheale* does not significantly differ from the respiratory lesion score found with the non-vaccinated animals.

Conclusion: a RecA-mutant and a PurD-mutant of *Ornithobacterium rhinotracheale*, if given as such, are not capable to raise a protective immune response in chickens.

Example 3

Comparison of Induction of Protection of Over-Attenuated *Ornithobacterium rhinotracheale* Strains after Priming and Boosting

TABLE 3 comparison of level of protection obtained with over-attenuated mutants after a first administration followed by a booster administration. Each group consisted of 12 chickens. Respiratory scores are given as a percentage of the maximally possible score of the challenged group. Challenge was done with wild-type

| Vacc. Day 1 $2 * 10^7$ CFU/ml strain RecA | Boost 2 weeks $2 * 10^7$ CFU/ml strain RecA | Prim. Day 23 | Chall. Day 28 A: $4 * 10^7$. Spray. | Resp. score. |
|---|---|---|---|---|
| — | — | NDV | A | 27 |
| Nostr./conj. 0.2 ml | Spray 100 ml | NDV | A | $19^b$ |

[b]not statistically different from non-vaccinated control.

Table 3 shows the result of a vaccination experiment in which chickens have been vaccinated first in the nostrils and then boosted after two weeks by spray-vaccination using a RecA-mutant of *Ornithobacterium rhinotracheale*. Priming was done with an NDV Lasota vaccine strain at day 23, and challenge with a wild-type *Ornithobacterium rhinotracheale* strain was done at day 28. The level of protection was determined by counting the respiratory lesions. As can be seen in the last column, the respiratory lesion score of the groups that received two subsequent vaccinations with a RecA-mutant of *Ornithobacterium rhinotracheale* does not significantly differ from the respiratory lesion score found with the non-vaccinated animals. Conclusion: a RecA-mutant of *Ornithobacterium rhinotracheale* is not capable, even when given twice, to raise a protective immune response in chickens.

Example 4

Induction of Lesions by Over-Attenuated Mutants and Wild-Type Strains

TABLE 4 comparison of induction of lesions by over-attenuated mutants and wild-type strains. Each group consisted of 12 chickens. Respiratory scores are given as a percentage of the maximally possible score of the challenged group.

| Prim. Day 23 | Chall. Day 28 100 ml spray | Resp. score. |
|---|---|---|
| NDV | RecA $7 * 10^7$ | 22 |
| NDV | PurD $2 * 10^8$ | 24 |
| NDV | Wild-type | 59 |

Table 4 shows the results of challenge with both an RecA-mutant, a PurD-mutant and a wild-type strain of *Ornithobacterium rhinotracheale*. No vaccination took place prior to priming and challenge. As can be seen from the last column, the mutants give a respiratory lesion score that is less than half the respiratory lesion score found after challenge with the wild-type strain. This clearly shows that the mutants behave mild, even without prior vaccination, and even after priming with a relatively "hot" NDV-strain, i.e. the Lasota strain.

Example 5

Comparison of Protection of *Ornithobacterium rhinotracheale*/NDV Combination Vaccines after Subsequent Challenge Experimental Design A 125 1-day-old SPF broiler chickens were used. At 1-day-old all chickens were spray vaccinated with live attenuated NDV and subsequently groups of 25 chickens were aerosol vaccinated with either of the mutant strains recA and purD or the wild type strain 3263/91 (serotype A) or were left unvaccinated (challenge controls). At 9 days after vaccination 10 chickens of each group were sacrificed for post-mortem examination to assess the safety of each vaccine. The remaining chickens (15 per group) were spray treated with ND-Lasota at 25-days of age and aerosol challenged with wild-type *Ornithobacterium rhinotracheale* 3263/91 (serotype A) at 31 days of age. Seven birds of each group were additionally challenged intravenously. At 38 days of age the chickens were killed and post-mortem examined to assess the efficacy of each vaccine.

In addition to a non-*Ornithobacterium rhinotracheale*-Vaccinated challenge control group, a non-*Ornithobacterium rhinotracheale*-vaccinated and non-challenged control group was used as NDV-control group.

The detailed experimental design and treatment schedule is shown in Table 5.

*Ornithobacterium rhinotracheale* Vaccine Cultures

For aerosol vaccination with the wild type *Ornithobacterium rhinotracheale* 3263/91 (serotype A), recA and purD, fresh cultures in Todd-Hewitt broth containing $6.7\times10^8$ CFU/ml, $3.9\times10^7$ CFU/ml and $2.6\times10^8$ CFU/ml, respectively, were used. The dose for aerosol vaccination was 100 ml per isolator.

ND Suspensions

NDV-strain NDC2 has been deposited at, and is obtainable as Nobilis NDC2/Nobilis Newhatch C2, or from the CNCM of the Institut Pasteur, 25 Rue du Docteur Roux, Paris, France under Accession number 1-1614. ND-Lasota was obtained from Intervet Int. B.V. (see above). The dose for NDC2 was $10^{6,4}$ $EID_{50}$ per animal (corresponding to 2 ml per bird) and for ND-Lasota $10^{6,6}$ $EID_{50}$ per animal (corresponding to 3 ml per bird), using a 1 L spray can.

*Ornithobacterium rhinotracheale* Challenge Culture

For aerosol challenge a fresh culture of wild-type *Ornithobacterium rhinotracheale* strain 3263/91 (serotype A) in Todd-Hewitt broth containing $4.3\times10^8$ CFU per ml (as determined by plate counting) was used.

Animals: 125 1-day-old SPF Hybro broilers were used.

Grouping and Dosing (Vaccination/Challenge)

Chickens were randomly divided (as they came to hand) over the different isolators and were treated as shown in Table 5.

NDC2 (1-day-old) or ND-Lasota (25-day-old) were given by spray using a 1 L spray can: 2 ml per bird or 3 ml per bird, respectively. The birds remained in the spray for 10 minutes with the air-circulation closed. At 1-day-old the birds were first treated with NDC2 and subsequently with *Ornithobacterium rhinotracheale*.

*Ornithobacterium rhinotracheale* vaccine (1-day-old) as well as *Ornithobacterium rhinotracheale* challenge (31-day-old) was given by aerosol at a dose of 100 ml per isolator using a paint sprayer.

After the aerosol challenge 7 birds of each group were additionally challenged intravenously at a dose of 1 ml into the wing vein.

Post Mortem Investigations

Birds that died during the experiment were subjected to a post-mortem examination to determine the cause of death.

At 10-day-old (9 days after vaccination) 10 birds per group were sacrificed and subjected to a post-mortem examination to assess the safety (attenuation) of the (vaccine) strains compared to the wild type. At 38 days of age (7 days after challenge) the (remaining) challenged birds were killed and also subjected to a post-mortem examination to assess the efficacy of the different strains.

The affection rates of the groups are given as a percentage of the maximal possible lesion score of the group.

Statistical Analysis

The total lesion scores per group (compared to the controls) were analysed two-sided using the non-parametric Mann-Whitney U test. The level of significance was set at 0.05.

Results and Conclusion

Concurrent aerosol vaccination at 1-day-old with live attenuated NDV and wild type *Ornithobacterium rhinotracheale* induced unacceptable lesions after vaccination but also (as a result of that) induced a strong protective response as evidenced after challenge where this group had the least post-mortem scores. Apparently, the initial lesions caused by the vaccination had already disappeared at time of challenge.

Concurrent aerosol vaccination at 1-day-old with live attenuated NDV and recA or purD mutant *Ornithobacterium rhinotracheale* strains demonstrated a good level of safety as well as efficacy.

As follows from Table 5, concurrent aerosol vaccination of 1-day-old SPF broilers with live attenuated NDV and recA or purD mutant strains appeared safe and to induce a good level of immunity against challenge with wild type *Ornithobacterium rhinotracheale.*

Example 6

Comparison of Protection of *Ornithobacterium rhinotracheale*/MA5 Combination Vaccines after Subsequent Challenge In this experiment, Infectious Bronchitisvirus type MA5 was used as the live attenuated viral component. Additionally, the experiment with *Ornithobacterium rhinotracheale*/NDV combination vaccines was repeated.

The experimental set-up of this Example was largely identical to that of Example 5. Where different numbers of animals or different moments of vaccination or challenge apply, this is indicated in Table 6. This table also gives an overview of the vaccines used and the vaccination schedule, as well as the level of protection obtained.

MA5 suspensions: live attenuated Infectious Bronchitisvirus (IBV) type MA5 (Intervet International B.V., Wim de Korverstraat 35, 5831 AN Boxmeer, The Netherlands) was used at a concentration of 5.5 $\log^{10}$ $EID_{50}$ per animal, and applied by spraying.

CONCLUSION

As follows from Table 6, concurrent aerosol vaccination of 1-day-old SPF broilers with IBV MA5 and PurD-mutant strains induces a good level of immunity against challenge with wild-type *Ornithobacterium rhinotracheale*. Additionally it follows from Table 6, that concurrent aerosol vaccination of 1-day-old SPF broilers with NCD and PurD-mutant strains induces a good level of immunity against challenge with wild-type *Ornithobacterium rhinotracheale* as was also demonstrated in Example 5.

Legend to the Figures

FIG. 1: cloning strategy for making mutation constructs of recA and purD genes in OR. Overlap extension PCR was used to create a deletion in the open reading frame of the gene of interest and these fragment were cloned in pUC19. Subsequently an antibiotic resistance marker gene (BamHI fragment) was cloned into the BglII site of the gene of interest (insertion-deletion constructs).

FIG. 2A: Sequence of purD and localization of primers used for cloning and verification of mutants. SEQ ID NO.: 9

FIG. 2B. Sequence of recA and localization of primers used for cloning and verification of mutants. SEQ ID NO.: 10

Table 5: Detailed experimental design and treatment schedule for the challenge experiment described in Example 5.

Table 6: Detailed experimental design and treatment schedule for the challenge experiment described in Example 6.

TABLE 5

| | | Treatment | | | | Results | |
|---|---|---|---|---|---|---|---|
| | | | | | | % of max | % of max |
| group | no. of chickens | vaccination at day 1 | | challenge at day 25 | challenge at day 31 | airsac score at day 10 (safety) | airsac score at day 38 (efficay) |
| 1 | 25 | NDV | RecA aerosol | NDV | WT-OR aerosol | 2.5 | 25[b] |
| 2 | 25 | NDV | PurD aerosol | NDV | WT-OR aerosol | 7.5 | 23[b] |
| 3 | 25 | NDV | WT-OR aerosol | NDV | WT-OR aerosol | 68 | 10[b] |
| 4 | 25 | NDV | | NDV | WT-OR aerosol | 0 | 47 |
| 5 | 25 | NDV | | NDV | | 0 | 2 |

[b]Significantly different ($p < 0.05$) compared to the controls (group 11) using two-sided Mann-Whitney U test

TABLE 6

| group | no. of chickens | Treatment vaccination at day 1 | | day 30 | challenge day 35 | Results % reduction |
|---|---|---|---|---|---|---|
| 1 | 15 | | PurD aerosol | NDV | WT-OR aerosol | no reduction |
| 2 | 15 | NDV | PurD aerosol | NDV | WT-OR aerosol | 54%[b] |
| 3 | 15 | NDV | | NDV | WT-OR aerosol | no reduction |
| 4 | 15 | MA5 | | NDV | WT-OR aerosol | no reduction |
| 5 | 15 | MA5 | PurD areosol | NDV | VT-OR aerosol | 50%[b] |

[b]Significantly different ($p < 0.05$) compared to the controls (group 11) using two-sided Mann-Whitney U test

The invention claimed is:

1. A combination vaccine for the protection of poultry against *Ornithobacterium rhinotracheale*, wherein said combination vaccine comprises a live over-attenuated *Ornithobacterium rhinotracheale* strain and a live attenuated poultry virus, and wherein said live, over attenuated *Ornithobacterium rhinotracheale* strain is not capable of inducing a protective immune response to *Ornithibacterium rhinotracheale* in animals primed with a virulent pathogen that predisposes the animal for infection with a secondary pathogenic bacterium.

2. The combination vaccine according to claim 1, wherein said live attenuated poultry virus is Infectious Bronchitis virus, Newcastle Disease virus, Turkey Rhinotracheitis virus, Marek's virus or Avian Reovirus.

3. The combination vaccine according to claim 1, wherein said live attenuated poultry virus is Infectious Bronchitis virus, Newcastle Disease virus or Turkey Rhinotracheitis virus.

4. The combination vaccine according to claim 1, wherein said live attenuated poultry virus is Newcastle Disease virus.

5. The combination vaccine according to claim 1, wherein said live attenuated poultry virus is Newcastle Disease virus type NDC2.

6. The combination vaccine according to claim 1, wherein said live attenuated poultry virus is Turkey Rhinotracheitis virus.

7. The combination vaccine according to claim 1, wherein said live attenuated poultry virus is Infectious Bronchitis virus.

8. The combination vaccine according to claim 1, wherein said live over-attenuated *Ornithobacterium rhinotracheale* has a mutation, said mutation preferably being a deletion in the purD-gene or the recA-gene that reduces the activity of those genes.

9. The combination vaccine according to claim 1, wherein said combination vaccine comprises an additional antigen from a virus or micro-organism pathogenic to poultry or genetic information encoding said antigen.

10. The combination vaccine according to claim 9, wherein the virus or micro-organism is selected from the group consisting of Infectious Bronchitis virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitisvirus, Duck Plague virus, Egg Drop syndrome virus, Infectious Laryngotracheitis virus, Herpes Virus of Turkeys, Eimeria species, *Ornithobacterium rhinotracheale, Pasteurella multocida, Mycoplasma synoviae, Salmonella* species and *E. coli.*

11. A method of protecting poultry against *Ornithobacterium rhinotracheale* comprising administering the combination vaccine of claim 1.

12. The method according to claim 11, wherein the live over-attenuated *Ornithobacterium rhinotracheale* strain and the live attenuated poultry virus are administered simultaneously, separately or sequentially.

13. A method for preparing the combination vaccine according to claim 1 wherein said method comprises the admixing of a live over-attenuated *Ornithobacterium rhinotracheale* strain, a live attenuated poultry virus and a pharmaceutically acceptable carrier.

14. A vaccination kit for the immunization of poultry against *Ornithobacterium rhinotracheale*, wherein said kit comprises a) a live over-attenuated *Ornithobacterium rhinotracheale* strain;

b) a live attenuated poultry virus;

c) a pharmaceutically acceptable carrier for (a); and d) a pharmaceutically acceptable carrier for (b).

15. A vaccination kit according to claim 14, wherein the carrier of (c) or (d) comprises an adjuvant.

* * * * *